United States Patent
Smith et al.

(10) Patent No.: US 12,114,840 B2
(45) Date of Patent: Oct. 15, 2024

(54) DNA COLLECTION DEVICE

(71) Applicant: SAPPHIROS LABORATORIES LLC, Boston, MA (US)

(72) Inventors: Robin Y. Smith, Boston, MA (US); Mike Robbat, Boston, MA (US)

(73) Assignee: SAPPHIROS LABORATORIES LLC, Boston, MA (US)

( * ) Notice: Subject to any disclaimer, the term of this patent is extended or adjusted under 35 U.S.C. 154(b) by 358 days.

(21) Appl. No.: 16/820,451

(22) Filed: Mar. 16, 2020

(65) Prior Publication Data

US 2020/0289098 A1   Sep. 17, 2020

Related U.S. Application Data (60) Provisional application No. 62/818,941, filed on Mar. 15, 2019.

(51) Int. Cl.
*A61B 10/02* (2006.01)
*C12N 15/10* (2006.01)

(52) U.S. Cl.
CPC .......... *A61B 10/02* (2013.01); *C12N 15/1003* (2013.01); *A61B 2010/0216* (2013.01)

(58) Field of Classification Search
None
See application file for complete search history.

(56) References Cited

U.S. PATENT DOCUMENTS

| | | | | |
|---|---|---|---|---|
| 4,951,684 A | * | 8/1990 | McMillan | A61B 10/02 600/571 |
| 5,462,063 A | * | 10/1995 | Kist | A61B 10/0291 600/570 |
| 6,258,044 B1 | * | 7/2001 | Lonky | A46B 3/18 600/562 |
| 6,464,939 B1 | * | 10/2002 | Bachand | B08B 1/003 600/572 |
| 8,475,394 B1 | * | 7/2013 | Stivers | A61B 10/02 600/572 |
| 9,750,483 B2 | * | 9/2017 | Weldon | A61B 10/02 |
| 2001/0026942 A1 | * | 10/2001 | Carpenter | A61B 10/0096 436/17 |
| 2002/0004019 A1 | * | 1/2002 | Bachand | B08B 1/003 435/287.7 |
| 2002/0120213 A1 | * | 8/2002 | Wallach | A61B 10/0291 600/569 |
| 2004/0181170 A1 | * | 9/2004 | Wallach | A61B 10/0291 600/572 |
| 2004/0214316 A1 | * | 10/2004 | O'Connell | C12M 45/22 435/309.1 |
| 2005/0252820 A1 | * | 11/2005 | Sanchez-Felix | A61B 10/0045 206/569 |
| 2007/0249961 A1 | * | 10/2007 | Morrison | A61F 13/38 600/572 |

(Continued)

*Primary Examiner* — Benjamin S Melhus
(74) *Attorney, Agent, or Firm* — Foley Hoag LLP; Erik Huestis; Lee Chedister (57) ABSTRACT

The disclosed technology relates generally to devices, kits, and related methods for collecting biological samples for genetic testing. In various embodiments, a DNA collection device for collecting cells from an orifice of a human subject includes an elongate arm. The DNA collection device further includes a swab head disposed at a distal end of the elongate arm, wherein the swab head is sized to at least partially enter the orifice, and wherein the swab head comprises a plurality of bristles disposed on a surface of the swab head.

9 Claims, 7 Drawing Sheets

(56) References Cited

U.S. PATENT DOCUMENTS

| | | | |
|---|---|---|---|
| 2008/0294067 A1* | 11/2008 | Zwart | A46D 1/0238 600/569 |
| 2010/0069791 A1* | 3/2010 | Ernster | A61B 10/02 600/569 |
| 2010/0125223 A1* | 5/2010 | Roan | A61B 10/02 600/569 |
| 2010/0137741 A1* | 6/2010 | Slowey | A61B 90/96 600/573 |
| 2013/0116596 A1* | 5/2013 | Birnboim | A61B 10/0096 600/572 |
| 2013/0267870 A1* | 10/2013 | Lonky | A61B 10/0291 600/569 |
| 2013/0338533 A1* | 12/2013 | Olsen | A61B 10/0291 600/569 |
| 2014/0336528 A1* | 11/2014 | Sethi | A61B 10/0266 600/566 |
| 2015/0164485 A1* | 6/2015 | Nickell | A61K 31/167 600/572 |
| 2015/0185228 A1* | 7/2015 | Reisacher | A61B 10/02 435/7.92 |
| 2015/0230872 A1* | 8/2015 | Lundkvist | A61B 90/98 600/572 |
| 2015/0315564 A1* | 11/2015 | Kindt | B65D 85/70 600/572 |
| 2016/0074022 A1* | 3/2016 | Oliva | A61B 10/0096 600/569 |
| 2016/0175838 A1* | 6/2016 | Lui | G01N 1/10 422/68.1 |
| 2016/0251724 A1* | 9/2016 | Ng | A61B 10/02 435/5 |
| 2017/0065261 A1* | 3/2017 | Ching | A61B 10/02 |
| 2018/0161022 A1* | 6/2018 | Baboolal | A61B 10/02 |
| 2019/0142642 A1* | 5/2019 | Burnet | A61B 5/445 600/362 |
| 2020/0017919 A1* | 1/2020 | Ng | C12Q 1/705 |
| 2020/0093467 A1* | 3/2020 | Lonky | A61B 17/32 |
| 2020/0229802 A1* | 7/2020 | Lonky | A61B 10/02 |
| 2021/0401408 A1* | 12/2021 | Holcombe | C12Q 1/689 |

* cited by examiner

DNA COLLECTION DEVICE

CROSS-REFERENCE TO RELATED APPLICATION

This application claims the benefit of U.S. Provisional Application No. 62/818,941, filed Mar. 15, 2019, which is hereby incorporated by reference in its entirety.

TECHNICAL FIELD

This application relates generally to devices, kits, and related methods for collecting biological samples, such as the collection of cells for genetic testing.

BACKGROUND

Modern diagnostic techniques have been proven capable of analyzing genetic material to provide unprecedented amounts of information regarding a human subject, for example, the ability to identify genetic mutations from extracted biological samples. Unfortunately, there are limitations to the collection of the extracted biological samples that compromise the possible results of the aforementioned diagnostic techniques, such as difficult or painful collection processes, poor patient compliance, ineffective collection methods, and storage/transport issues.

As such, there is a need for an easy and effective method of collecting biological samples for use in a diagnostic process.

BRIEF SUMMARY

Generally, this disclosure relates to improved devices and related kits and methods for collecting cellular material that can be used for genetic testing. In particular, the disclosure relates to swabs (e.g., buccal swabs) including bristles that extend from a surface of the swab for effectively harvesting the cellular material from, for example, the inside of a human subject's check. However, the device is not limited to collecting buccal cells or to use on human subjects.

Text. In one aspect, the invention is directed to a DNA collection device for collecting cells (e.g., buccal epithelial cells) from an orifice (e.g., a mouth) of a human subject, the device comprising: an elongate arm; and a swab head disposed at a distal end of the elongate arm, wherein the swab head is sized to at least partially enter the orifice (e.g., wherein the swab head is sufficiently small to at least partially enter the orifice), and wherein the swab head comprises a plurality of bristles disposed on a surface of the swab head.

In certain embodiments, the orifice is a mouth and the swab head is configured to collect buccal cells, e.g., wherein the swab head is sufficiently small to enter the mouth. In various embodiments, the swab head is sufficiently small to fit comfortably within the mouth to thereby provide for collection of buccal cells.

In certain embodiments, at least a portion of the plurality of bristles are packed together to form one or more bristle sets (e.g., packed together in one or more substantially circular regions having a diameter of about 3 mm to about 4 mm). In certain embodiments, the bristles of the one or more bristle sets are of a substantially same length, packed in close proximity (e.g., separated by no more than about a diameter of an individual bristle), and extend outwards in substantially a same direction from the surface (e.g., a substantially planar surface) of the swab head (e.g., such that tips of the bristles lie substantially in a plane and form a substantially flat bristled surface). In certain embodiments, at least a portion of the one or more bristle sets are oriented to correspond to a spacing of wells on at least a portion of a well plate (e.g., a 96 well plate or a 384 well plate). In certain embodiments, at least a portion of the one or more bristle sets are evenly spaced on a surface of the swab head.

In certain embodiments, the swab head is sufficiently small to fit within a conical centrifuge tube. In various embodiments, the swab head may have a cross-sectional diameter of about 1 mm to 50 mm, about 5 mm to 30 mm, or about 10 mm to 20 mm. In various embodiments, the swab head may have a height of about 10 mm to 150 mm, about 20 mm to 100 mm, or about 25 mm to 50 mm.

In certain embodiments, the swab head has a substantially cylindrical shape and at least a portion of the plurality of bristles are disposed on a circumferential surface thereof (e.g., and extend radially outwards from the circumferential surface).

In certain embodiments, the device further comprises a protective sleeve removably disposed about at least the swab head. In certain embodiments, the protective sleeve comprises: a removable hood; and a base disposed about and secured to at least a portion of the elongate arm, wherein the base is operable to sealingly engage with the hood (e.g., wherein the base comprises an opening substantially similar in shape and size to an opening of the hood, with which the hood sealingly engages).

In another aspect, the invention is directed to a DNA collection kit comprising: a single use collection device (e.g., the collection device of any one of the aspects and embodiments described herein) for collecting cells (e.g., buccal epithelial cells) from an orifice of a human subject, the device comprising: an elongate arm; and a swab head disposed at a distal end of the elongate arm, wherein the swab head is sized to at least partially enter the orifice, and wherein the swab head comprises a plurality of bristles disposed on a surface of the swab head; and a containment device comprising a housing for the collection device.

In certain embodiments, the kit comprises instructions for using the DNA collection kit. In certain embodiments, the containment device comprises a re-closable return sleeve. In certain embodiments, the kit comprises a prepaid return envelope.

In certain embodiments, the kit further comprises a foldable box for shipping the kit to a consumer. In certain embodiments, the foldable box is configured to be refolded (e.g., wherein the foldable box comprises a sheet of foldable material comprising (i) a top surface and (ii) a plurality of folds, wherein the sheet is shaped and sized, and the plurality of folds are positioned, to provide a folded and unfolded configuration of the box) to support return shipment by the consumer.

In certain embodiments, the kit further comprises a registration card for transmitting information on a human subject.

In another aspect, the invention is directed to a method of collecting DNA from a human subject, the method comprising the steps of: a) obtaining a collection device (e.g., the collection device of any one of the aspects and embodiments described herein) comprising an elongate arm and a swab head disposed at a distal end of the elongate arm, the swab head comprising a plurality of bristles disposed on a surface of the swab head; b) exposing the swab head of the collection device by removing the collection device from a first sealed container; c) inserting the swab head within an orifice (e.g., a mouth) of the human subject, wherein the plurality of bristles is oriented toward a collection site (e.g., an interior surface of the mouth, or an internal surface of a cheek) within the orifice; d) firmly moving the swab head over the collection site; e) removing the swab head from the orifice; and f) placing the collection device in a second sealed container.

In certain embodiments, the orifice is a mouth, the collection site is an internal surface of a cheek (e.g., and the swab head is moved about 20 times over substantially the entire internal surface).

In certain embodiments, the method further comprises the step of aerating the swab for approximately 30 seconds prior to inserting in the second sealed container.

In certain embodiments, the first and second sealed containers are the same containers.

In certain embodiments, the method further comprises the step of placing the sealed second container in to a prepaid return envelope.

In another aspect, the invention is directed to a method of extracting DNA from a collection device, the method comprising the steps of: a) obtaining a test sample from a subject, wherein the test sample is disposed on a collection device (e.g., the collection device of any one of the aspects and embodiments described herein) comprising an elongate arm and a swab head disposed at a distal end of the elongate arm, the swab head comprising a plurality of bristles for extracting (e.g., from the subject) and holding the test sample; b) exposing the test sample; c) positioning the collection device relative to a collection receptacle (e.g., a well plate, such as a 96 well plate, or a collection vial, such as a conical centrifuge tube); and d) transferring the test sample to the collection receptacle.

In certain embodiments, the collection receptacle is a well plate (e.g., a 96 well plate and/or a 384 well plate) comprising at least one or more wells.

In certain embodiments, the step of positioning the collection device comprises positioning the collection device relative to the well plate, such that at least a portion of the plurality of bristles holding the test sample are aligned with the at least one or more wells of the well plate.

In certain embodiments, the step of transferring the test sample comprises inserting at least a portion of the plurality of bristles into the at least one or more wells of the well plate.

In certain embodiments, the step of exposing the test sample comprises removing the collection device from a sealed container.

In certain embodiments, the method further comprises a step of assaying the test sample. In certain embodiments, the step of assaying the test samples comprises performing one or more genetic test measurements (e.g., genotyping measurements, such as a TaqMan® assay) to generate genotyping data.

In another aspect, the invention relates to a single use DNA collection device for collecting cells (e.g., buccal epithelial cells) from an orifice (e.g., a mouth) of a human subject. The device includes an elongate arm and a swab head disposed at a distal end of the elongate arm. The swab head is configured to at least partially enter the orifice and includes one or more sets of bristles disposed on a surface of the head. In some embodiments, the orifice is a mouth and the device is configured to collect buccal cells. In some embodiments, the swab head is relatively small, for example, no larger than 1.5 inches along a first dimension, no larger than 0.5 inches along a second dimension, and no larger than 0.75 inches along a third dimension.

In various embodiments, each of the one or more sets of bristles has a cross-sectional diameter of about 0.5 mm to about 10 mm, preferably about 1 mm to about 5 mm, and more preferably about 3 mm to about 4 mm. The cross-section of each set of bristles may be circular, ovoid, square, rectangular, or a variant of any of the foregoing. In certain embodiments, the cross-section of each set of bristles has a characteristic dimension (e.g., a characteristic length, width, or diameter) of about 3 mm to about 4 mm such that the bristle set can fit into a well of a well plate (e.g., a microtiter plate, or a 96-well plate).

In certain embodiments, the plurality of bristles comprises one or more sets of bristles, each comprising a plurality of bristles of a substantially same length, packed in close proximity, and extending outwards in substantially a same direction from a substantially planar surface of the swab head. The plurality of bristles within the bristle set may be separated from one another by no more than about a diameter of an individual bristle. The extension of the plurality of bristles outward from the swab head in the substantially same direction from the planar surface of the swab head may be such that the tips of the plurality of the bristles would lie substantially in a plane and form a substantially flat, bristled surface.

In certain embodiments, the swab head is sufficiently small enough to fit within a conical centrifuge tube. The conical centrifuge tube having a cross-sectional diameter of about 1 mm to 50 mm, preferably about 5 mm to 30 mm, and more preferably about 10 mm to 20 mm. The conical centrifuge tube having a depth of 10 mm to 150 mm, preferably about 20 mm to 100 mm, more preferably about 25 mm to 50 mm.

In certain embodiments, there is a plurality of sets of bristles disposed on the surface of the swab head. In some embodiments, the bristle sets can be generally arranged in a grid or table arrangement comprising a set of rows and columns. In a particular embodiment, the bristle sets are arranged to correspond to a spacing of wells on a well plate, such as a 96 well plate or a portion thereof, such that the cellular material can be more directly transferred to the interior of the well plate. In some embodiments, a distance between the centers of each row and each column of bristle sets can be, for example, about 9 mm and may vary depending on the geometry of the well plate. Alternatively or additionally, the swab head has a substantially cylindrically shape and the at least one set of bristles is oriented about a circumferential surface of the swab head. In some embodiments, the at least one set of bristles comprises a plurality of sets of bristles disposed along a length of the circumferential surface of the swab head.

In some embodiments, the plurality of bristle sets includes about two (2) to about forty (40) bristle sets, preferably about two (2) to about twenty (20) bristles sets. In some embodiments the sets are evenly spaced on the surface of the swab head. In some embodiments, the swab head includes six (6) bristle sets arranged in two (2) horizontal rows of three (3) bristle sets relative to the elongate arm in a horizontal orientation. However, other numbers and arrangements of bristle sets is contemplated and considered within the scope of the invention. For example, in some embodiments, there are about two (2) to about ten (10) rows of two (2) bristle sets disposed along a circumferential surface of a curved swab head. In some embodiments, the at least one set (or each set) of bristles includes about two (2) to about sixty (60) bristles, preferably about two (2) to about forty (40) bristles, and more preferably about two (2) to about twenty (20) bristles. In various embodiments, the at least one set of bristles extends from the surface of the swab head about 0.3 mm to about 10 mm, preferably about 0.5 mm to about 6 mm, and more preferably about 0.5 mm to about 3 mm.

In additional embodiments, the bristles can be made of a synthetic material, such as a nylon or a polyester, or a natural material, such as animal hairs. In some embodiments, the at least one set of bristles include bristles with tapered ends and/or bristles of a soft, medium or firm hardness, which can be uniform through the set of bristles or vary between bristles or along the lengths of the bristles. Additionally, the swab head can have a substantially rectangular shape; however, other shapes are contemplated and considered within the scope of the invention to suit a particular application (for example, type of cells to be collected and type of orifice). For example, in some embodiments, the shape of the swab head is substantially cylindrical and either curved or straight. The device can also include a protective sleeve removably disposed about at least the swab head. The sleeve can sealingly engage the swab head or the entire device as needed to maintain a sterile or aseptic condition of the device. In some embodiments, the protective sleeve includes a removable hood and a base disposed about and secured to at least a portion of the elongate arm, where the base is configured to sealingly engage with the hood and the hood may be disposed about the swab head.

In another aspect, the invention relates to a DNA collection kit. The kit includes a collection device, a containment device configured for housing the collection device, and instructions for using the kit. The collection device is configured to collect cells from an orifice of a human subject and includes an elongate arm and a swab head disposed at a distal end of the elongate arm. The swab head is configured to at least partially enter the orifice and includes at least one set of bristles disposed on a surface of the head.

In various embodiments, the containment device includes a re-closable return sleeve, such as the sleeve described above. In some embodiments, the sleeve may also be configured for shipping the collection device. For example, the containment device can include postage and an address label. Additionally, the kit could include a separate prepaid return envelope. In some embodiments, the kit includes a foldable box for shipping the kit to a consumer, where the foldable box can be refolded or otherwise reconfigured to facilitate return shipment. In some embodiments, the foldable box can include printed materials (e.g., instructions for use) on a surface of the box or other functionality to assist with the collection of the sample. In some embodiments, the kit also includes a registration card configured for transmitting information on a human subject. For example, the registration card and any contained data can be transmitted via the return envelope or include means for transmitting the data via the internet (e.g., scanned and emailed or manually entered via a web portal). Additionally, the kit may include means for securing the various contents therein, such as an adhesive, elastic straps, or perforated slits.

In another aspect, the invention relates to a method of collecting DNA, or other biological material, from a human subject. The method includes the steps of: obtaining a collection device, where the device includes an elongate arm and a swab head disposed at a distal end of the elongate arm; exposing the at least one swab head of the collection device by, for example, removing the collection device from a first sealed container; inserting the swab head within an orifice of the human subject such that at least one set of bristles disposed on the swab head is oriented toward (i.e., so as to be engagable with) a collection site (e.g., exposed tissue on a surface of the orifice); firmly moving the swab head over the collection site; removing the swab head from the orifice; and placing the collection device in a second sealed container.

In various embodiments, the orifice is a mouth and the collection site is an internal surface of one or both cheeks; however, other bodily orifices are contemplated and considered within the scope of the invention. Typically, the swab head is firmly moved about twenty (20) times over substantially the entire internal surface, for example, the inside of both cheeks. In some embodiments, additional steps may be taken prior to collecting the sample, such as cleaning the collection site. For example, if the collection site is the inside of a cheek, the subject should rinse their mouth with water or other solution, preferably two or more times to eliminate, or at least reduce, the possibility of collecting a contaminated sample. The method can also include aerating the swab (e.g., waving the collection device in the air) for approximately 30 seconds prior to inserting in to the sealed container. The aeration time may vary depending the collection site and type of sample collected.

In additional embodiments, the first and second sealed containers are the same containers. For example, the first container could include a detachable sleeve that sealingly engages a base member and can be detached by grasping the opposite ends of the collection device and pulling. The collection device can then be inserted into the sleeve, which can be resealed to the base member. In some embodiments, there is a second container, such as a sealable plastic bag into which the collection device can be inserted, either with or without the original sleeve reattached. Additionally, the method includes the step of placing the sealed second container in to a prepaid return envelope, which can then be deposited with any USPS mail box or other delivery service. In some embodiments the method includes a registration step that may include one or more of: filling out a registration card that can be sent back with the collection device; downloading an app; or manually entering data via a web portal.

In another aspect, the invention relates to a method of extracting DNA from a collection device. In one embodiment, the collection device includes an elongate arm and a swab head disposed at a distal end of the elongate arm. The swab head can include at least one set of bristles that are configured for holding a test sample. The method includes the steps of: obtaining the test sample from a subject, where the test sample is disposed on the collection device; exposing the test sample; positioning the collection device relative to a collection receptacle, such as a well plate, slide, conical tube, or similar; and transferring the test sample to the piece of collection receptacle. In various embodiments, the step of positioning the collection device includes positioning the collection device relative to a well plate, such that the at least one set of bristles holding the test sample is aligned with at least one well within the well plate; and the step of transferring the test sample includes inserting the at least one set of bristles into the at least one well. Alternatively, the test sample can be transferred to a well plate, slide, test tube, or other media.

In various embodiments of the foregoing aspect, the step of exposing the test sample includes removing the collection device from a sealed container (e.g., by removing from a sterile container, such as a plastic bag or sealable sleeve) and possibly first removing the sealed collection device from a shipping envelope. In some embodiments, the collection device includes a plurality of sets of bristles arranged in a grid or table pattern and the step of positioning the collection device relative to a well plate includes aligning the plurality of sets of bristles with a plurality of wells within the well plate, such as a 96 well plate. In some embodiments, the method further includes the step of inserting each of the plurality of sets of bristles in each of the plurality of wells simultaneously. The method may include repeating the various method steps until the well plate is filled (i.e., all of the wells are used). For example, if the collection device has six (6) evenly spaced sets of bristles (e.g., two rows of 3 or three rows of 2) and a 96 well plate is used, it would be possible to extract DNA from up to sixteen (16) different collection devices. The method can also include assaying the test samples. In certain embodiments, the assaying includes performing one or more genetic test measurements to generate genotyping data. In some embodiments, these test measurements may include genotyping measurements such as a TaqMan® assay.

These and other objects, along with advantages and features of the disclosed systems and methods, will become apparent through reference to the following description and the accompanying drawings. Furthermore, it is to be understood that the features of the various embodiments described are not mutually exclusive and can exist in various combinations and permutations.

Definitions

In order for the present disclosure to be more readily understood, certain terms are first defined below. Additional definitions for the following terms and other terms are set forth throughout the specification.

As used herein, the term "approximately" or "about," as applied to one or more values of interest, refers to a value that is similar to a stated reference value. In certain embodiments, the term "approximately" or "about" refers to a range of values that fall within 25%, 20%, 19%, 18%, 17%, 16%, 15%, 14%, 13%, 12%, 11%, 10%, 9%, 8%, 7%, 6%, 5%, 4%, 3%, 2%, 1%, or less in either direction (greater than or less than) of the stated reference value unless otherwise stated or otherwise evident from the context (except where such number would exceed 100% of a possible value).

As used herein, the term "subject" refers to any organism from which a biological sample is or may be obtained, e.g., for experimental, diagnostic, prophylactic, cosmetic, and/or therapeutic purposes. Typical subjects include animals (e.g., mammals such as mice, rats, rabbits, non-human primates, and/or humans). In certain embodiments, a subject is a human.

As used herein, the term "substantially" refers to the qualitative condition of exhibiting total or near-total extent or degree of a characteristic or property of interest.

Unless defined otherwise, technical and scientific terms have the same meaning as commonly understood by one of ordinary skill in the art to which this invention belongs.

BRIEF DESCRIPTION OF THE DRAWINGS

In the drawings, like reference characters generally refer to the same parts throughout the different views. Also, the drawings are not necessarily to scale, emphasis instead generally being placed upon illustrating the principles of the disclosed systems and methods and are not intended as limiting. For purposes of clarity, not every component may be labeled in every drawing. In the following description, various embodiments are described with reference to the following drawings, in which.

DETAILED DESCRIPTION

As described herein, illustrative embodiments provide devices, kits, and methods useful for collecting cellular material for DNA testing, specifically from the buccal cavity.

Figure 1:
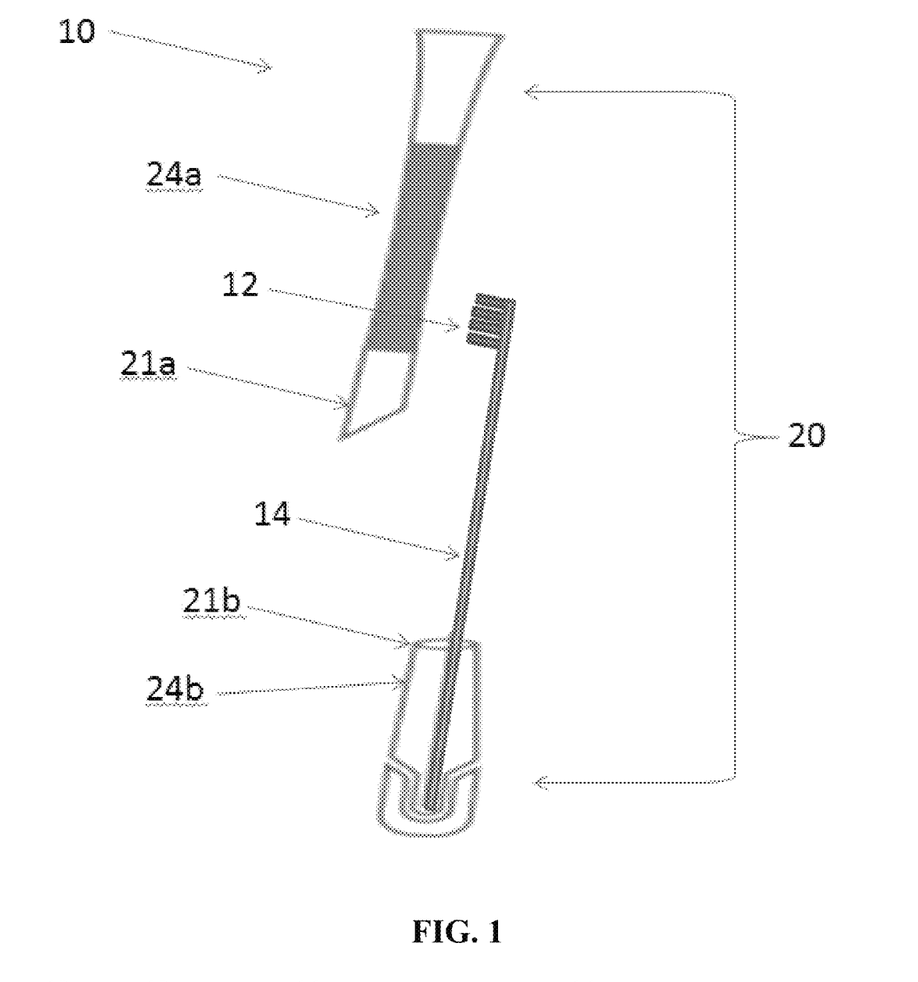
FIG. 1 is a partially exploded perspective view of a DNA collection device in accordance with one or more embodiments of the invention.

FIG. 1 depicts one embodiment of a collection device 10 having an elongate body or arm 14 with a swab head 12 disposed at a distal end thereof. In some embodiments, the swab head 12 and elongate arm 14 may be formed as a single piece (e.g., via injection molding) or the swab head 12 can be a separate piece that is either permanently affixed to or releasably attached to the elongate arm 14. Also depicted is a container 20 for isolating the collection device from the environment (e.g., to keep it sterile or at least uncontaminated).

As shown, the container has two parts; a base section 24b secured to the elongate arm 14 and a removable sleeve 24a sealingly engaged therewith. The base section 24b can be secured to the elongate arm 14 by bonding or could be slidably engaged with the arm 14 to provide for other functionality. In various embodiments, the mating ends 21a, 21b of the sleeve 24a and base 24b will have means for attachment, separation, and reattachment. For example, the ends could include an adhesive with a bonding strength that can be overcome by a user pulling the two parts away from each other, but also resilient enough so that the ends 21a, 21b can be reattached to isolate the device 10 and sample from the environment. The sleeve 24a will typically have a slightly flexible structure. Alternatively or additionally, the ends 21a, 21b could include an interlock structure (e.g., threads or a pin and slot arrangement) to reversibly secure the two parts 24a, 24b. The device 10 can be made from one or more polymeric materials; however, other materials are contemplated and considered within the scope of the invention.

As shown, for example in FIG. 1, swab head 12 comprises a plurality of bristles disposed thereon. The bristles extend outwards from the surface of the swab head and facilitate collection of genetic material from a subject. They may, for example, facilitate collection of buccal cells, by, e.g., facilitating scraping of cells off of an inside of a cheek of a subject.

In certain embodiments, the swab head 12 is rectangular, and the bristles extend outwards from a substantially flat and/or planar surface. In certain embodiments, the swab head is cylindrical in shape, and the bristle extend outwards in a radial fashion.

Figure 2:
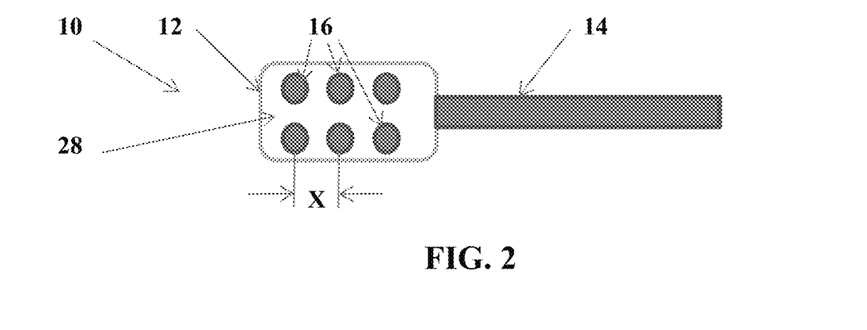
FIG. 2 is an enlarged plan view of a portion of the device of FIG. 1 in accordance with one or more embodiments of the invention.

FIG. 2 depicts one example of a rectangular swab head 12 in greater detail; however, as previously noted, the swab head can be substantially cylindrical in shape and curved or straight to suit a particular application (e.g., sample site, size or shape of diagnostic equipment). In certain embodiments, sets of bristles are packed together to form one or more bristle sets. For example, the swab head 12 includes a plurality of bristle sets 16 that are secured to the swab head 12 and extend from a surface 28 thereof. Six bristle sets 16 are depicted in FIG. 2; however, a single bristle set or as many as sixty bristle sets 16 can be disposed on the swab head 12.

In certain embodiments, the bristle sets are arranged to facilitate deposition of genetic material collected using device 10 into a well plate, such as a 96 well plate. For example, as shown in FIG. 2, the plurality of bristle sets 16 can be arranged in a grid or table-like pattern (i.e., with a predetermined number of rows and columns) and oriented to correspond to and interface with the wells on a well plate. In various embodiments, the plurality of bristle sets 16 may be arranged such that each bristle set 16 is aligned with (or aligns with) a well on a well plate. In various embodiments, where a rectangular swab head is used, a user may align the bristle sets 16 with the wells on a well plate and insert the bristle sets 16 into the well plate simultaneously to thereby deposit any collected material into the well plates. In various embodiments, where a cylindrical swab head is used, only some of the bristle sets (e.g., a single row) may be inserted into wells (e.g., a single row) of a well plate at any time. In various embodiments, the bristle sets 16 of a cylindrical swab head may be arranged such that rotation of the swab head (along with some horizontal translation of the collection device) will align the next row of bristle sets 16 into the next row/column of wells on the well plate. In some embodiments, the bristle sets 16 are oriented so the device 10 can be used with a 96 well plate, where a spacing "X" between the bristle sets 16 is about 9 mm. The spacing is typically the same in the vertical and horizontal directions. In various embodiments, the bristle sets 16 have a substantially circular arrangement and an overall cylindrical shape; however other shapes are contemplated and may be used in accordance with the devices, kits and methods described herein. In some embodiments, the diameter of each bristle set is about 3 mm to about 4 mm and the bristles extend about 1 mm from the surface 28 of the swab head 12. In some embodiments, the bristles have substantially the same lengths such that the ends of the bristles define a substantially planar top surface. However, the lengths of individual bristles and/or sets of bristles can vary to suit a particular application. For example, in some embodiments, the bristle lengths may vary to form a rounded top surface, as opposed to a planar surface, to better correspond to the topography of a collection site.

Each bristle set can include about five to ten individual bristles bundled together (e.g., in a single column attached to the swab head or folded in half to provide a large diameter bristle set) and secured to the swab head 12 via bonding or mechanical fasteners. In one embodiment, each bristle set is disposed within an opening in the surface 28 of the swab head 12 and held in place via an interference fit, an adhesive, or both. Additionally, the exposed ends of the bristles can have a flat, tapered, or otherwise shaped configuration as needed to suit a particular application (e.g., type of orifice or tissue to be collected or the configuration of the wells within the well plate). In some embodiments, the bristles may be coated or otherwise treated in a manner to improve the hold between the bristles and the collected material and/or preserve the DNA.

Figure 3:
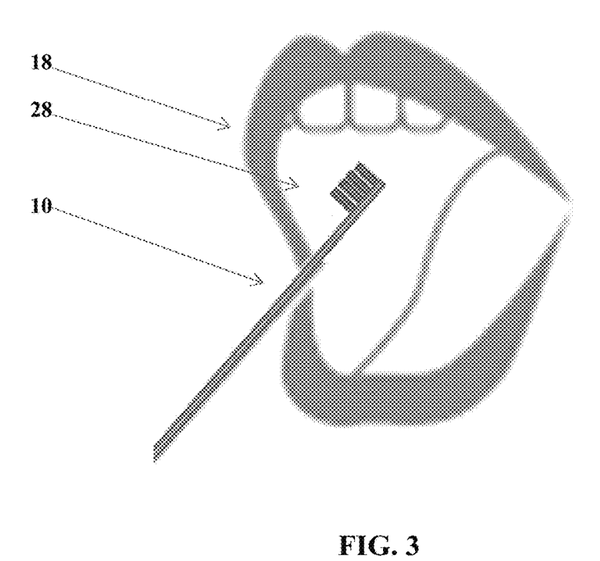
FIG. 3 is a perspective view of a DNA collection device deployed within an orifice of a human subject in accordance with one or more embodiments of the invention.

FIG. 3 depicts the device 10 in use. In this case, the orifice 18 is a mouth of a human subject and the collection site 28 is an internal surface of the cheek. The device 10 is inserted at least partially within the orifice 18, for example, the swab head 12 and a portion of the elongate arm 14. The device 10 is oriented so that the bristles 16 face the collection site 28. In some embodiments, the collection site is an internal surface of a lumen and the device 10 can be rotated as needed to collect cells from the entire surface. In use, for example, collecting buccal cells, the swab head 12 is rubbed firmly against substantially the entire surface of the cheek approximately twenty (20) times and then repeated on the other cheek. Generally, the bristles 16 will collect and hold the cellular material removed from the collection site 28. Because of the nature of the bristles 16, the collection of cellular material is more robust, as the bristles will typically collect a greater amount of material and are less sensitive to user issues, such as insufficient pressure or generally poor collection technique.

Figure 4:
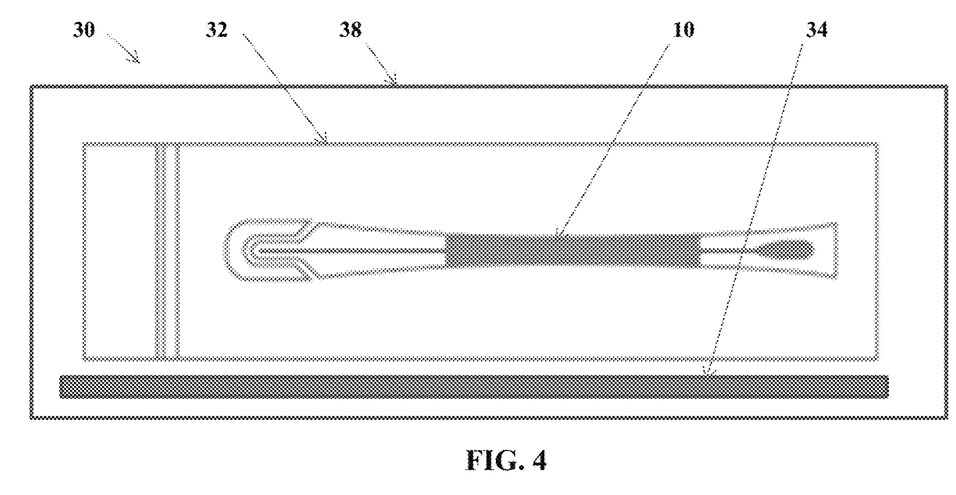
FIG. 4 is a plan view of a DNA collection kit in accordance with one or more embodiments of the invention.
Figure 5:
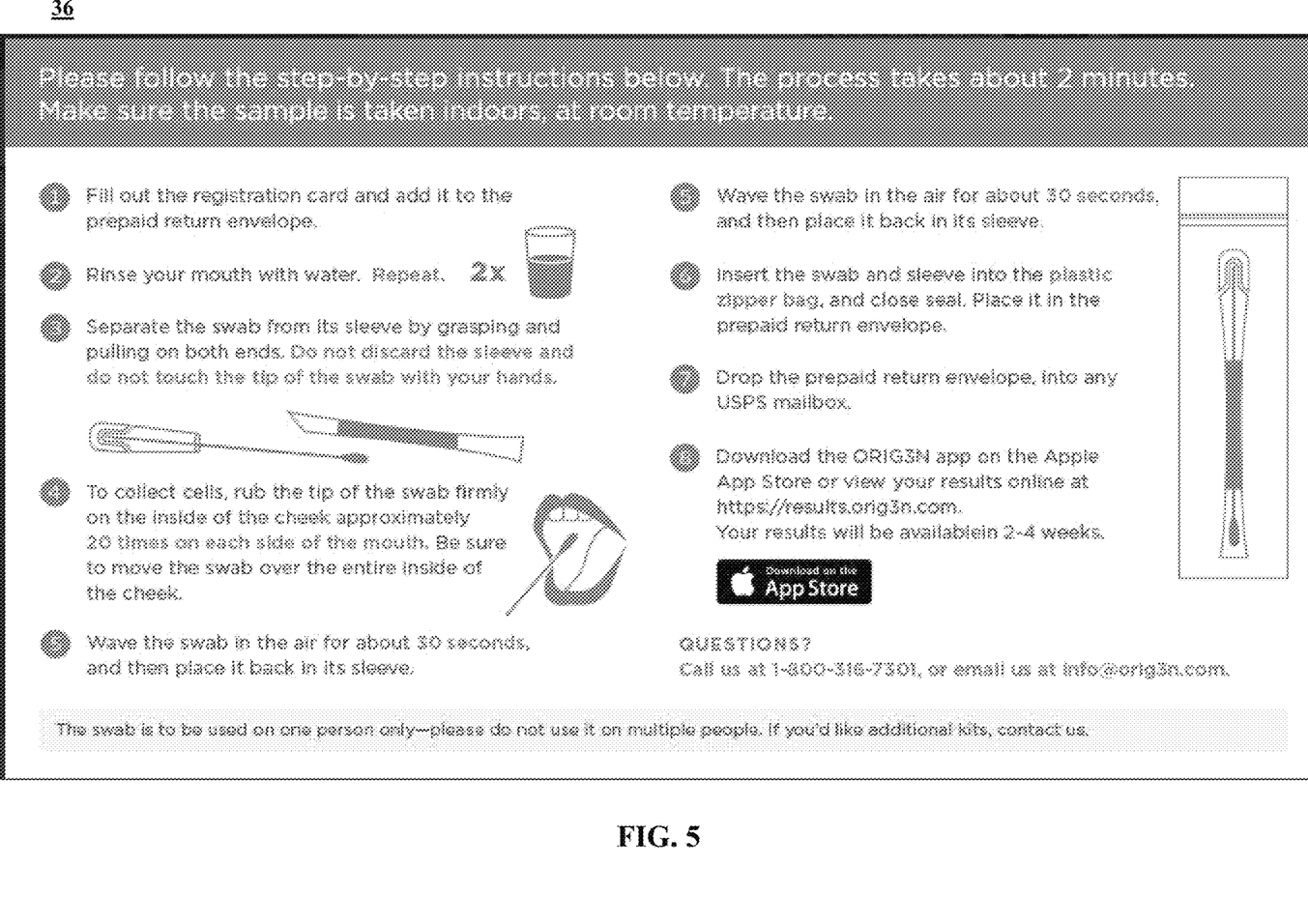
FIG. 5 is a plan view of a set of instructions included with a DNA collection kit in accordance with one or more embodiments of the invention.

FIG. 4 depicts one embodiment of a test kit 30 that a consumer can purchase and have sent to themselves for use at their convenience. As shown, the kit 30 includes a shipping container 38, such as a foldable box described below. The container 38 holds the device 10, shown here in a resealable plastic envelope 32, a prepaid return envelope 34, and an instruction card 36 (see FIG. 5). In some embodiments, the instruction card 36 is a separate item within the container 38, but it could also be printed on or otherwise affixed to a surface of the container 38. The kit 30 may also include a registration card or other identification means that can be returned with the device 10 once the cells have been collected.

Figure 6:
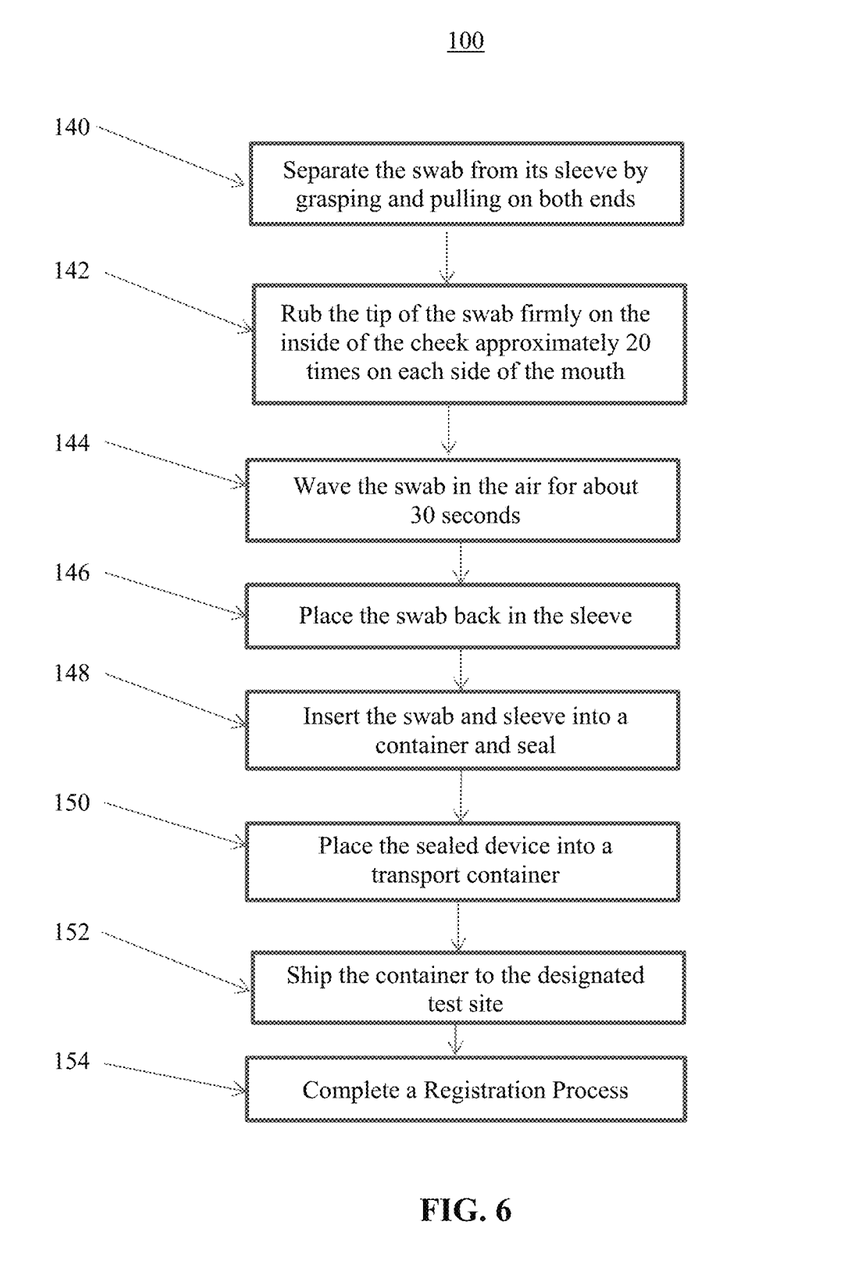
FIG. 6 is a flow chart illustrating the various steps of using the disclosed DNA collection device in accordance with one or more embodiments of the invention.

FIG. 6 depicts the various steps of a method 100 of using the device 10. Generally, once a consumer receives the kit, they will open the container 38 and verify the contents. The consumer will remove the device and proceed according to the instructions. The first step 140 includes exposing the device for use by removing its protective sleeve. In one embodiment, this is done by grasping both ends of the device and pulling, which will release the sleeve from the device (e.g., mating base) and expose the swab head. The sleeve should be retained as it is reusable. In some embodiments, the consumer has to first remove the device 10 from the resealable envelope 32. Next, the consumer rubs the swab head firmly against a collection site approximately twenty (20) times in step 142. In this example, the collection site is the inside of the cheek and the device is collecting buccal cells.

Step 144 is directed to aerating the swab head, typically by waving the device in the air, to help secure the cellular material to the device. The consumer than places the device back within the sleeve, which is resealable with the base, in step 146. In step 148, the consumer than inserts the used collection device into the resealable envelope, which is typically a plastic zipper bag; however, other resealable containers may be used. Next, the consumer places the device and associated package into a container for transport to, for example, a laboratory in step 150. In some embodiments, the transport container is the prepaid return envelope 34 that may be included in the kit 30. In other embodiments, the container may be the foldable box 38 that can be reconfigured for return shipment (e.g., an inner surface may have a return address and prepaid postage printed thereon that become an outer surface when the box is folded into a different configuration). Step 152 involves shipping the container back, which can be as simple as dropping the container into any USPS mailbox.

The registration step 154 is depicted as a final step; however, the basic registration process can occur at almost any point during the method 100 and in some embodiments may include multiple steps carried out at different stages. For example, in some embodiments, the registration process is as simple as filling out a registration card that gets included in the transport container. In some embodiments, the registration card will include a preprinted identifier to assist in the processing of the sample. In some embodiments, the registration process may include additional or alternative steps involving downloading an app, entering information via a web portal, or both.

Figure 7:
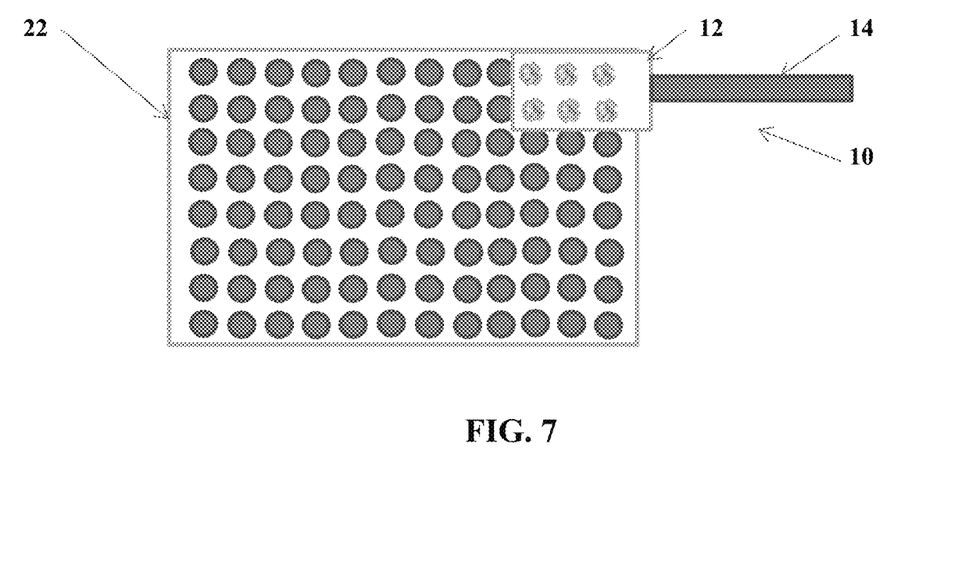
FIG. 7 is a plan view of one embodiment of a DNA collection device engaging with a well plate in accordance with one or more embodiments of the invention.

FIG. 7 depicts a possible process for transferring the collected sample to a piece of diagnostic equipment, specifically the interaction between the device 10 and a well plate 22.

Figure 8:
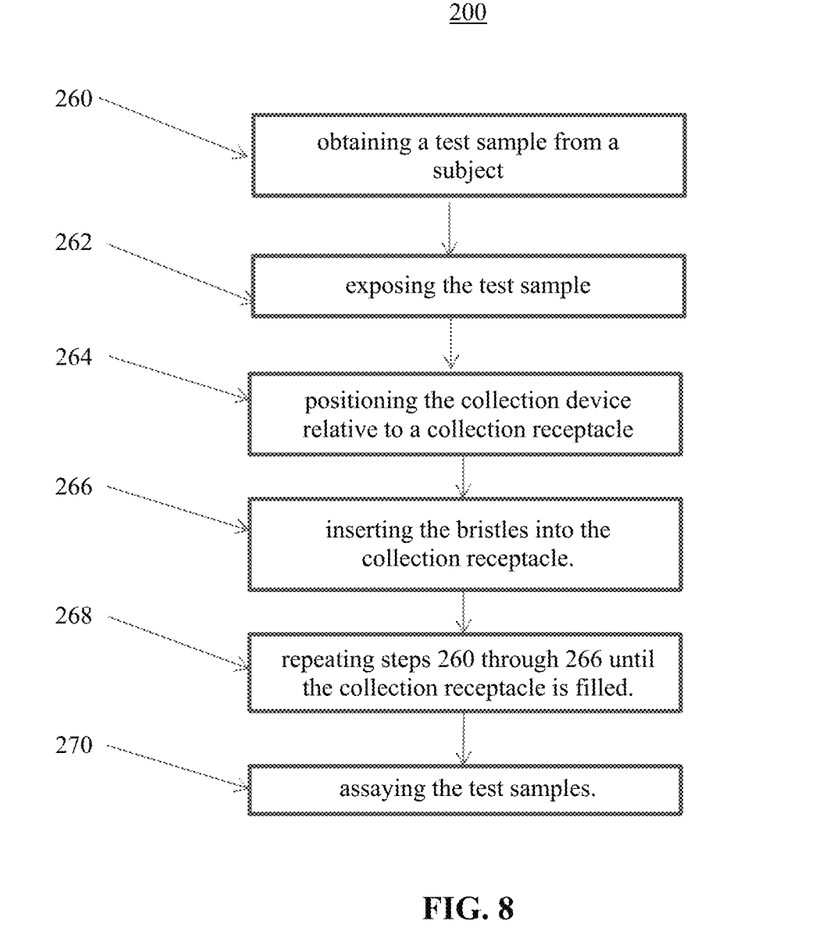
FIG. 8 is a flow chart illustrating the various steps of extracting the cellular material from the device in accordance with one or more embodiments of the invention.

FIG. 8 depicts the method 200 of extracting the DNA sample from the collection device 10 and delivering it to a collection receptacle, such as a conical centrifuge tube, a well-plate, etc., so that it can be assayed.

Referring to FIG. 8, a laboratory or other processing facility will obtain the test sample from the consumer (i.e., human subject), or in some cases from an intermediate party, as shown in step 260. Next, the laboratory/technician will remove the device from the packaging to expose the collection device in step 262. Once the device is free of the packaging, the device is positioned relative to a collection receptacle in step 264. For example, the device can be loaded into a machine that automates the entire processing, including moving the device relative to the collection receptacle. In some embodiments, the method can be carried out manually. Once the device is in position (see FIG. 7), the device (e.g., the bristles of the swab head) can be inserted into the collection receptacle 266.

In certain embodiments, wherein the collection receptacle comprises multiple collection regions, bristle sets of the device are oriented such that the device can be lowered into the collection receptacle and each of the bristle sets holding the cellular material will enter into a single collection region, such as a single well in step 266. For example, as described above and shown in FIG. 7, the size, shape, and orientation of the bristle sets correspond to the structure of a well plate, such as a 96 well plate, to minimize errors in transferring the samples to the well plate. In some embodiments, the well plates are prepared to accept specific types of cellular material or assist in the transfer of the cellular material to the well plate (e.g., each well may include an agar gel or other solution to which the material/bristles are brought into contact).

Depending on the size of the well plate and the configuration of the device, the technician may repeat steps 260-266 for additional test samples until the well plate is filled and ready for processing (optional step 268). Alternatively, any diagnostic tests can be carried out on a single device sample. In step 270, the test sample(s) are assayed for, for example, genotyping, sequencing, etc. In some embodiments, the samples are genotyped to analyze genetic variants, such as single nucleotide polymorphisms (SNPs), or large structural changes in DNA. Generally, once completed, the collection devices are disposed of in a proper manner.

In certain embodiments, the DNA collection device described herein can be used collect genetic material to perform genetic tests to obtain genotyping data for a subject. The obtained genotyping data can be used to generate personal genetic profiles for a subject, in order to inform them about their unique genetic makeup and how it relates to their physical traits and characteristics, for example as described in PCT/US17/67264 (published as WO2018/118892, entitled "SYSTEMS AND METHODS FOR CREATION OF PERSONAL GENETIC PROFILE PRODUCTS"), filed Dec. 19, 2017, the content of which is hereby incorporated by reference in its entirety. Extraction of genetic material and assay workflows to perform genetic tests from samples obtained using the DNA collection devices, methods, and kits described herein may include sample tracking and processing approaches such as those described in PCT/US17/67272 (published as WO 2018/190914, entitled "CHAIN OF CUSTODY FOR BIOLOGICAL SAMPLES AND BIOLOGICAL MATERIAL USED IN GENOTYPING TESTS"), filed Dec. 19, 2017, the content of which is hereby incorporated by reference in its entirety.

The DNA collection devices and kits described herein may be included in a sample collection kit provided to a customer, via an initial purchase as well as, in certain embodiments, through a follow up kit, sent once a reserve of the customer's genetic material is determined to be low and in need of replenishment. Examples of systems and methods for monitoring and replenishing reserves of genetic material, which may be used in combination with the DNA collection devices, kits, and methods described herein are described in PCT/US18/16377 (published as WO 2018/144691, entitled "SYSTEMS AND METHODS FOR AUTOMATED MONITORING AND REPLENISHMENT OF GENETIC MATERIAL RESERVES"), filed Feb. 1, 2018, the content of which is hereby incorporated by reference in its entirety. Examples of a foldable box system, which may be used in combination with the DNA collection devices, kits, and methods described herein, are described in PCT/US19/39735 (published as WO2020/009920, entitled "FOLDABLE BOX FOR GENETIC ASSESSMENT KIT"), filed on Jun. 28, 2019 and in U.S. Design Appln. No. 29/655,776, filed Jul. 6, 2018 (Appendix E).

Definitions

In order for the present disclosure to be more readily understood, certain terms are first defined below. Additional definitions for the following terms and other terms are set forth throughout the specification.

As used herein, the term "approximately" or "about," as applied to one or more values of interest, refers to a value that is similar to a stated reference value. In certain embodiments, the term "approximately" or "about" refers to a range of values that fall within 25%, 20%, 19%, 18%, 17%, 16%, 15%, 14%, 13%, 12%, 11%, 10%, 9%, 8%, 7%, 6%, 5%, 4%, 3%, 2%, 1%, or less in either direction (greater than or less than) of the stated reference value unless otherwise stated or otherwise evident from the context (except where such number would exceed 100% of a possible value).

As used herein, the term "subject" refers to any organism from which a biological sample is or may be obtained, e.g., for experimental, diagnostic, prophylactic, cosmetic, and/or therapeutic purposes. Typical subjects include animals (e.g., mammals such as mice, rats, rabbits, non-human primates, and/or humans). In certain embodiments, a subject is a human.

As used herein, the term "substantially" refers to the qualitative condition of exhibiting total or near-total extent or degree of a characteristic or property of interest.

Unless defined otherwise, technical and scientific terms have the same meaning as commonly understood by one of ordinary skill in the art to which this invention belongs.

Figure 9:
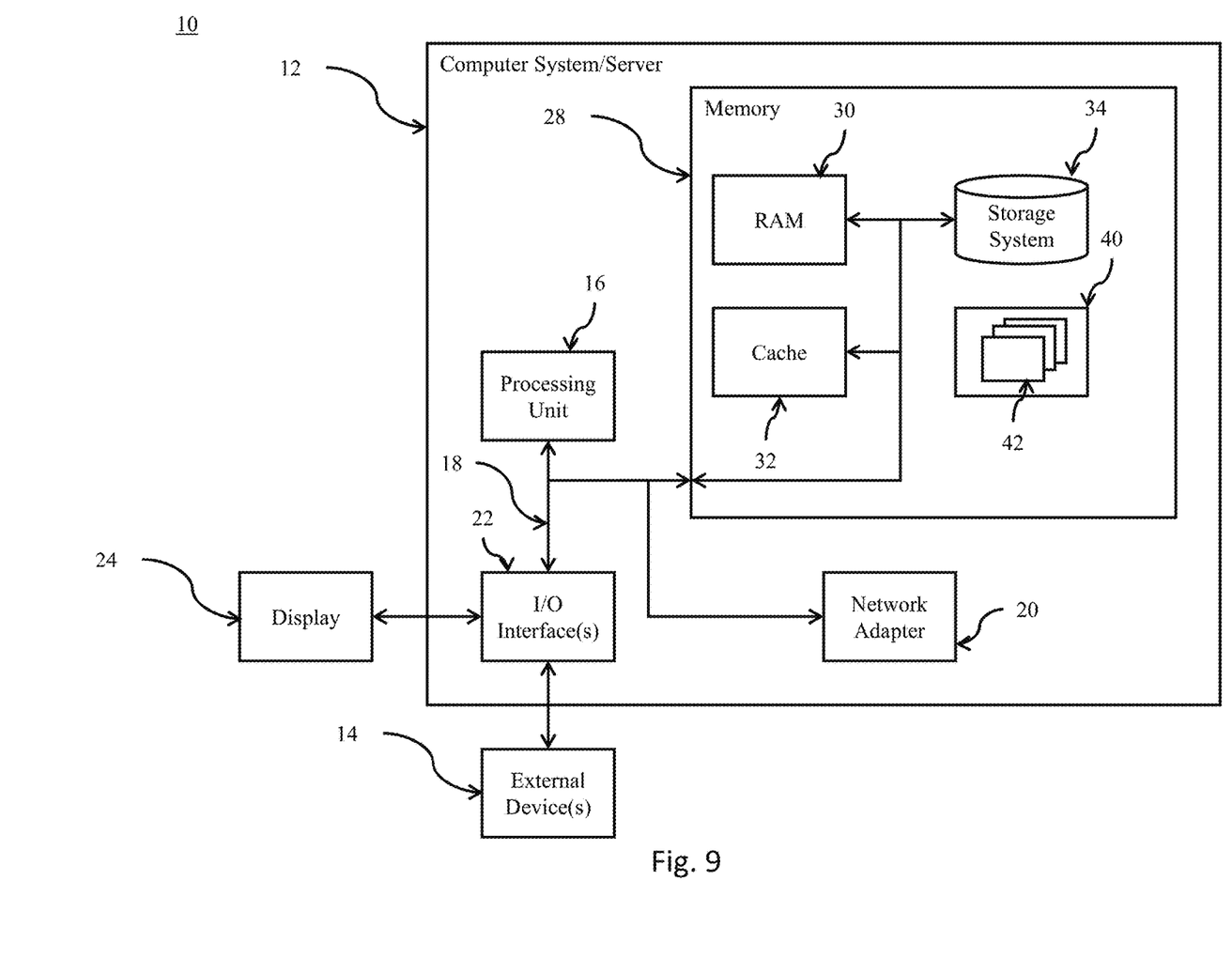
FIG. 9 depicts an exemplary computing node according to embodiments of the present disclosure.

With reference to FIG. 9, a schematic of an example of a computing node is shown. Computing node 10 is only one example of a suitable computing node and is not intended to suggest any limitation as to the scope of use or functionality of embodiments of the invention described herein. Regardless, computing node 10 is capable of being implemented and/or performing any of the functionality set forth hereinabove.

In computing node 10 there is a computer system/server 12, which is operational with numerous other general purpose or special purpose computing system environments or configurations. Examples of well-known computing systems, environments, and/or configurations that may be suitable for use with computer system/server 12 include, but are not limited to, personal computer systems, server computer systems, thin clients, thick clients, handheld or laptop devices, multiprocessor systems, microprocessor-based systems, set top boxes, programmable consumer electronics, network PCs, minicomputer systems, mainframe computer systems, and distributed cloud computing environments that include any of the above systems or devices, and the like.

Computer system/server 12 may be described in the general context of computer system-executable instructions, such as program modules, being executed by a computer system. Generally, program modules may include routines, programs, objects, components, logic, data structures, and so on that perform particular tasks or implement particular abstract data types. Computer system/server 12 may be practiced in distributed cloud computing environments where tasks are performed by remote processing devices that are linked through a communications network. In a distributed cloud computing environment, program modules may be located in both local and remote computer system storage media including memory storage devices.

As shown in FIG. 9, computer system/server 12 in computing node 10 is shown in the form of a general-purpose computing device. The components of computer system/server 12 may include, but are not limited to, one or more processors or processing units 16, a system memory 28, and a bus 18 that couples various system components including system memory 28 to processor 16.

Bus 18 represents one or more of any of several types of bus structures, including a memory bus or memory controller, a peripheral bus, an accelerated graphics port, and a processor or local bus using any of a variety of bus architectures. By way of example, and not limitation, such architectures include Industry Standard Architecture (ISA) bus, Micro Channel Architecture (MCA) bus, Enhanced ISA (EISA) bus, Video Electronics Standards Association (VESA) local bus, and Peripheral Component Interconnect (PCI) bus.

Computer system/server 12 typically includes a variety of computer system readable media. Such media may be any available media that is accessible by computer system/server 12, and it includes both volatile and non-volatile media, removable and non-removable media.

System memory 28 can include computer system readable media in the form of volatile memory, such as random access memory (RAM) 30 and/or cache memory 32. Computer system/server 12 may further include other removable/non-removable, volatile/non-volatile computer system storage media. By way of example only, storage system 34 can be provided for reading from and writing to a non-removable, non-volatile magnetic media (not shown and typically called a "hard drive"). Although not shown, a magnetic disk drive for reading from and writing to a removable, non-volatile magnetic disk (e.g., a "floppy disk"), and an optical disk drive for reading from or writing to a removable, non-volatile optical disk such as a CD-ROM, DVD-ROM or other optical media can be provided. In such instances, each can be connected to bus 18 by one or more data media interfaces. As will be further depicted and described below, memory 28 may include at least one program product having a set (e.g., at least one) of program modules that are configured to carry out the functions of embodiments of the invention.

Program/utility 40, having a set (at least one) of program modules 42, may be stored in memory 28 by way of example, and not limitation, as well as an operating system, one or more application programs, other program modules, and program data. Each of the operating system, one or more application programs, other program modules, and program data or some combination thereof, may include an implementation of a networking environment. Program modules 42 generally carry out the functions and/or methodologies of embodiments of the invention as described herein.

Computer system/server 12 may also communicate with one or more external devices 14 such as a keyboard, a pointing device, a display 24, etc.; one or more devices that enable a user to interact with computer system/server 12; and/or any devices (e.g., network card, modem, etc.) that enable computer system/server 12 to communicate with one or more other computing devices. Such communication can occur via Input/Output (I/O) interfaces 22. Still yet, computer system/server 12 can communicate with one or more networks such as a local area network (LAN), a general wide area network (WAN), and/or a public network (e.g., the Internet) via network adapter 20. As depicted, network adapter 20 communicates with the other components of computer system/server 12 via bus 18. It should be understood that although not shown, other hardware and/or software components could be used in conjunction with computer system/server 12. Examples, include, but are not limited to: microcode, device drivers, redundant processing units, external disk drive arrays, RAID systems, tape drives, and data archival storage systems, etc.

The present disclosure may be embodied as a system, a method, and/or a computer program product. The computer program product may include a computer readable storage medium (or media) having computer readable program instructions thereon for causing a processor to carry out aspects of the present disclosure.

The computer readable storage medium can be a tangible device that can retain and store instructions for use by an instruction execution device. The computer readable storage medium may be, for example, but is not limited to, an electronic storage device, a magnetic storage device, an optical storage device, an electromagnetic storage device, a semiconductor storage device, or any suitable combination of the foregoing. A non-exhaustive list of more specific examples of the computer readable storage medium includes the following: a portable computer diskette, a hard disk, a random access memory (RAM), a read-only memory (ROM), an erasable programmable read-only memory (EPROM or Flash memory), a static random access memory (SRAM), a portable compact disc read-only memory (CD-ROM), a digital versatile disk (DVD), a memory stick, a floppy disk, a mechanically encoded device such as punch-cards or raised structures in a groove having instructions recorded thereon, and any suitable combination of the foregoing. A computer readable storage medium, as used herein, is not to be construed as being transitory signals per se, such as radio waves or other freely propagating electromagnetic waves, electromagnetic waves propagating through a waveguide or other transmission media (e.g., light pulses passing through a fiber-optic cable), or electrical signals transmitted through a wire.

Computer readable program instructions described herein can be downloaded to respective computing/processing devices from a computer readable storage medium or to an external computer or external storage device via a network, for example, the Internet, a local area network, a wide area network and/or a wireless network. The network may comprise copper transmission cables, optical transmission fibers, wireless transmission, routers, firewalls, switches, gateway computers and/or edge servers. A network adapter card or network interface in each computing/processing device receives computer readable program instructions from the network and forwards the computer readable program instructions for storage in a computer readable storage medium within the respective computing/processing device.

Computer readable program instructions for carrying out operations of the present disclosure may be assembler instructions, instruction-set-architecture (ISA) instructions, machine instructions, machine dependent instructions, microcode, firmware instructions, state-setting data, or either source code or object code written in any combination of one or more programming languages, including an object oriented programming language such as Smalltalk, C++ or the like, and conventional procedural programming languages, such as the "C" programming language or similar programming languages. The computer readable program instructions may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider). In some embodiments, electronic circuitry including, for example, programmable logic circuitry, field-programmable gate arrays (FPGA), or programmable logic arrays (PLA) may execute the computer readable program instructions by utilizing state information of the computer readable program instructions to personalize the electronic circuitry, in order to perform aspects of the present disclosure.

Aspects of the present disclosure are described herein with reference to flowchart illustrations and/or block diagrams of methods, apparatus (systems), and computer program products according to embodiments of the disclosure. It will be understood that each block of the flowchart illustrations and/or block diagrams, and combinations of blocks in the flowchart illustrations and/or block diagrams, can be implemented by computer readable program instructions.

These computer readable program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks. These computer readable program instructions may also be stored in a computer readable storage medium that can direct a computer, a programmable data processing apparatus, and/or other devices to function in a particular manner, such that the computer readable storage medium having instructions stored therein comprises an article of manufacture including instructions which implement aspects of the function/act specified in the flowchart and/or block diagram block or blocks.

The computer readable program instructions may also be loaded onto a computer, other programmable data processing apparatus, or other device to cause a series of operational steps to be performed on the computer, other programmable apparatus or other device to produce a computer implemented process, such that the instructions which execute on the computer, other programmable apparatus, or other device implement the functions/acts specified in the flowchart and/or block diagram block or blocks.

The descriptions of the various embodiments of the present disclosure have been presented for purposes of illustration, but are not intended to be exhaustive or limited to the embodiments disclosed. Many modifications and variations will be apparent to those of ordinary skill in the art without departing from the scope and spirit of the described embodiments. The terminology used herein was chosen to best explain the principles of the embodiments, the practical application or technical improvement over technologies found in the marketplace, or to enable others of ordinary skill in the art to understand the embodiments disclosed herein.

What is claimed is:

1. A DNA collection device for collecting cells from an orifice of a human subject, the device comprising:
    an elongate arm;
    a well plate having a plurality of wells with a first spacing between each well; and
    a swab head disposed at a distal end of the elongate arm, wherein the swab head is sized to at least partially enter the orifice, and wherein the swab head comprises a plurality of bristle sets disposed on a surface of the swab head, each bristle set within the plurality of bristle sets comprising one or more bristles bundled together, the bristles within each bristle set separated by no more than a bristle diameter, and wherein the bristle sets have the same first spacing as the well plate.

2. The device of claim 1, wherein the orifice is a mouth and the swab head is configured to collect buccal cells.

3. The device of claim 1, wherein the bristles of the bristle sets are of a same length, and extend outwards in a same direction from the surface of the swab head.

4. The device of claim 1, wherein the bristle set has a length corresponding to a depth of the wells in the well plate.

5. A DNA collection kit comprising: the DNA collection device of claim 4; and a containment device comprising a housing for the collection device.

6. The device of claim 1, wherein at least a portion of the bristle sets are evenly spaced on a surface of the swab head.

7. The device of claim 1, wherein the swab head has a cylindrical shape and at least a portion of the plurality of bristle sets are disposed on a circumferential surface thereof.

8. The device of claim 1, further comprising a protective sleeve removably disposed about at least the swab head.

9. The device of claim 8, wherein the protective sleeve comprises: a removable hood; and
a base disposed about and secured to at least a portion of the elongate arm, wherein the base is operable to sealingly engage with the hood.

\* \* \* \* \*